(12) United States Patent
Frach et al.

(10) Patent No.: US 8,476,594 B2
(45) Date of Patent: *Jul. 2, 2013

(54) TEMPERATURE COMPENSATION CIRCUIT FOR SILICON PHOTOMULTIPLIERS AND OTHER SINGLE PHOTON COUNTERS

(75) Inventors: Thomas Frach, Aachen (DE); Gordian Prescher, Cologne (DE); Carsten Degenhardt, Aachen (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 132 days.

This patent is subject to a terminal disclaimer.

(21) Appl. No.: 13/139,307

(22) PCT Filed: Nov. 19, 2009

(86) PCT No.: PCT/IB2009/055186
§ 371 (c)(1),
(2), (4) Date: Jun. 13, 2011

(87) PCT Pub. No.: WO2010/070487
PCT Pub. Date: Jun. 24, 2010

(65) Prior Publication Data
US 2011/0248175 A1    Oct. 13, 2011

Related U.S. Application Data

(60) Provisional application No. 61/122,476, filed on Dec. 15, 2008.

(51) Int. Cl.
 G01T 1/164    (2006.01)
 G01T 1/20    (2006.01)
(52) U.S. Cl.
 USPC ............ 250/363.03; 250/370.08; 250/370.09; 250/370.1; 250/370.11; 250/363.04

(58) Field of Classification Search
 USPC ............ 250/370.08–370.11, 370.15, 363.03, 250/363.04, 338.1–338.4
 See application file for complete search history.

(56) References Cited

U.S. PATENT DOCUMENTS 3,904,818 A    9/1975  Kovac
4,438,348 A    3/1984  Casper et al.
(Continued)

FOREIGN PATENT DOCUMENTS

JP    63187672 A    8/1988
JP    01302190 A    12/1989
WO    2006111883 A2    10/2006

OTHER PUBLICATIONS

Liu et al., "Low Dark Count Rate and High Single-Photon Detection Efficiency Avalanche Photodiode in Geiger-Mode Operation", Mar. 6, 2007, IEE Photonics Technology Letter, vol. 19, No. 6, pp. 378-380.*

(Continued)

*Primary Examiner* — David Porta
*Assistant Examiner* — Jeremy Valentiner

(57) ABSTRACT

A PET scanner (8) includes a ring of detector modules (10) encircling an imaging region (12). Each of the detector modules includes at least one detector pixel (24,34). Each detector pixel includes a scintillator (20, 30) optically coupled to one or more sensor APDs (54) that are biased in a breakdown region in a Geiger mode. The sensor APDs output a pulse in response to the light from the scintillator corresponding to a single incident radiation photon. A reference APD (26, 36) also biased in a break-down down region in a Geiger mode is optically shielded from light and outputs a temperature dependent signal. At least one temperature compensation circuit (40) adjusts a bias voltage applied to the sensor APDs based on the temperature dependent signal.

18 Claims, 5 Drawing Sheets

U.S. PATENT DOCUMENTS

| | | | |
|---|---|---|---|
| 4,792,997 A | 12/1988 | Toussaint et al. | |
| 5,696,657 A | 12/1997 | Nourrcier, Jr. et al. | |
| 6,894,266 B2 * | 5/2005 | Richard et al. | 250/214 R |
| 7,381,958 B2 * | 6/2008 | Karp et al. | 250/363.03 |
| 2004/0245436 A1 | 12/2004 | Matsumoto | |
| 2007/0096033 A1 * | 5/2007 | Freund et al. | 250/370.11 |
| 2007/0187611 A1 * | 8/2007 | Chowdhury et al. | 250/370.14 |
| 2008/0156993 A1 * | 7/2008 | Weinberg et al. | 250/363.03 |
| 2010/0226495 A1 * | 9/2010 | Kelly et al. | 380/30 |
| 2011/0291017 A1 * | 12/2011 | Frach | 250/366 |

OTHER PUBLICATIONS

Kataoka, J., et al.; An active gain-control system for Avalanche photo-diodes under moderate temperature variations; 2006; Nuclear Instruments and Methods in Physics Research; A 564(1):300-307.

\* cited by examiner

TEMPERATURE COMPENSATION CIRCUIT FOR SILICON PHOTOMULTIPLIERS AND OTHER SINGLE PHOTON COUNTERS

CROSS REFERENCE TO RELATED APPLICATIONS

This application claims the benefit of U.S. provisional application Ser. No. 61/122,476 filed Dec. 15, 2008, which is incorporated herein by reference.

The following relates to the nuclear radiation detector arts. It finds particular application in conjunction with radiation detectors for nuclear medical imagers employing radiation transmission or radiopharmaceuticals, such as single photon emission computed tomography (SPECT) imagers, positron emission tomography (PET) imagers, planar x-ray imagers, and the like, and will be described with particular reference thereto. It will be appreciated that the invention may also be applicable to other radiation imaging modalities, and in systems and methods employing radiation detectors such as astronomy and airport luggage screening.

In single-photon emission computed tomography (SPECT), a radiopharmaceutical is administered to an imaging subject, and one or more radiation detectors, commonly called gamma cameras, are used to detect the radiopharmaceutical via radiation emission caused by radioactive decay events. Typically, each gamma camera includes a radiation detector array and a honeycomb collimator disposed in front of the radiation detector array. The honeycomb collimator defines a linear or small-angle conical line of sight so that the detected radiation comprises projection data. If the gamma cameras are moved over a range of angular views, for example over a 180° or 360° angular range, then the resulting projection data can be reconstructed using filtered back-projection, expectation-maximization, or another imaging technique into an image of the radiopharmaceutical distribution in the imaging subject. Advantageously, the radiopharmaceutical can be designed to concentrate in selected tissues to provide preferential imaging of those selected tissues.

In positron emission tomography (PET), a radiopharmaceutical is administered to the imaging subject, in which the radioactive decay events of the radiopharmaceutical produce positrons. Each positron interacts with an electron to produce a positron-electron annihilation event that emits two oppositely directed gamma rays. Using coincidence detection circuitry, a ring array of radiation detectors surrounding the imaging subject detect the coincident oppositely directed gamma ray events corresponding to the positron-electron annihilation. A line of response (LOR) connecting the two coincident detections contains the position of the positron-electron annihilation event. Such lines of response are analogous to projection data and can be reconstructed to produce a two- or three-dimensional image. In time-of-flight PET (TOF-PET), the small time difference between the detection of the two coincident γ ray events is used to localize the annihilation event along the LOR (line of response).

In planar x-ray imaging, a radiation source irradiates an imaging subject, and a radiation detector array disposed on the opposite side of the imaging subject detects the transmitted radiation. Due to attenuation of radiation by tissues in the imaging subject, the detected radiation provides a two-dimensional planar representation of bones or other hard, radiation-absorbing structures in the imaging subject. Such transmission-based imaging is improved upon in transmission computed tomography imaging, in which the x-ray tube or other radiation source is revolved around the imaging subject to provide transmission views or projection data over an extended angular range, for example over a 180° or 360° span of angular views. Using filtered back-projection or another image reconstruction technique, this radiation projection data is reconstructed into a two- or three-dimensional image representation.

SPECT, PET, and other radiation-based medical imaging share a common need for compact and robust radiation detector modules. Such radiation detector modules are also used in other areas such as astronomy and luggage screening. In the past, SPECT and PET radiation detector modules have typically consisted of an array of photomultiplier tubes (PMT's) optically coupled with scintillator crystals. The scintillator crystal converts the absorbed radiation particle into a light burst which is measured by the photomultiplier tubes. Photomultiplier tubes are stable and provide high gain (~$10^6$) characteristics but they are bulky, fragile, require high voltages, and are very sensitive to magnetic fields. In some radiation detection systems, the photomultiplier tubes have been replaced by photodiodes that produce an analog signal proportional to the intensity of the light bursts. Even though photodiodes offer a cost-effective, low voltage alternative to photomultiplier tubes in high light situations, they do not provide the adequate gain in low light (low gamma ray flux) sensing applications, thus leading to poor signal-to-noise ratios.

To address these difficulties, silicon photomultipliers (SiPM) detectors have been developed which incorporate the high gain and stability of photomultiplier tubes along with the cost-effective, low voltage nature of the analog photodiodes. SiPM detectors use a pixilated array of small avalanche photodiodes (APDs) that are each optically coupled to a corresponding scintillation crystal. The APDs are biased in the breakdown region. In this region, the APDs become sensitive to single carriers. These carriers, electrons and/or holes, can be either thermally generated, thus leading to the dark counts that cause noise, or photo-generated by absorption of single or multiple photons in the sensitive region of the diode. Both electrons and holes can initiate the breakdown of the diode, thereby producing a strong output signal. A passive or active recharge circuit, located approximate to each diode, resets the diode to the sensitive state after a breakdown event. In analog SiPMs, the output signal consists of the cumulative charge of a large number of passively quenched diodes. In contrast, digital SiPMs detect breakdown events individually based on voltage pulses that are digitized by logic gates and counted by digital counters that are located approximate to the APDs.

In digital Geiger-mode, APDs break down in response to a photon of light from a radiation event in the corresponding scintillation crystal and produce an output pulse. The output pulse functioning as binary 1's are counted to determine the number of photons generated by the radiation event striking the corresponding scintillator. This photon count corresponds to the energy of the detected radiation event.

While sensitive to individual photon events, breakdown voltage of each APD is affected by operating temperature. Assuming constant biasing conditions, temperature-induced drift of the breakdown voltage leads to a corresponding change of the excess voltage. Photon detection is affected by changes in excess voltage because: (1) the charge pulse produced during breakdown is proportional to the product of the diode capacitance and the excess voltage, and (2) the excess voltage determines the field strength inside the device, thus leading to a drift of the photon detection probability. Analog SiPMs, which count detected photons as a measured charge signal, are affected by both factors and become very sensitive to temperature. In contrast, in voltage sensing digital SiPMs, the voltage pulse must exceed the gate level threshold to be detected and so this type of SiPM is only affected by the drift of the photon detection probability. However, a drift of the photon detection probability can still reduce the energy resolution of the detector. Since the dark current rate (DCR) is doubled every 8° C., to reduce the noise (DCR) of the sensor and avoid errors due to temperature variations in the APDs, proposals have been made to cool the detectors. For air cooling, air flow passages are provided through the detector increasing bulk. Even with air cooling, temperature fluctuations can occur. Liquid cooling can be more effective, but adds complexity to the system. Even with liquid cooling, some fluctuations can occur.

The present application contemplates a new and improved nuclear imaging detector module apparatus and method which overcomes the above-referenced problems and others.

In accordance with one aspect, a radiation detector module for use in diagnostic imaging is provided. The module has at least one detector pixels, each including a scintillator optically coupled to one or more avalanche photodiodes that are biased in a breakdown region in a Geiger mode. The sensor avalanche photodiodes are configured to output a pulse in response to light from the scintillator corresponding to a single incident radiation photon. At least one reference detector is configured to output a temperature dependent signal. At least one temperature compensation circuit is configured to adjust a bias voltage applied to the sensor avalanche photodiodes based on the temperature dependent signal.

In accordance with another aspect, a PET scanner is provided. The scanner includes a plurality of radiation detector elements as described above encircling an imaging region. A coincidence detector detects pairs of detected radiation events and determines lines of response corresponding to the coincident pairs. A reconstruction processor reconstructs the lines of response into an image representation.

In accordance with another aspect, a method of compensating for temperature changes of a radiation detector is provided. Output pulses are generated from sensor avalanche photodiodes which are biased in a breakdown region in a Geiger mode in response to light from an associated scintillator causing one or more of the sensor avalanche photodiodes to break down. A temperature dependent signal is generated in accordance with a sensed temperature of the sensor avalanche photodiodes. A bias voltage applied to the sensor avalanche photodiodes is adjusted based on the temperature dependent signal.

In accordance with another aspect, a method of making a radiation detector module is provided. An array of avalanche photodiodes is formed. Sensor avalanche photodiodes of the array are optically coupled with scintillators. A reference avalanche photodiode of the array is formed on the same substrate in the same process as the sensor avalanche photodiodes. The reference avalanche photodiode is optically shielded. The reference avalanche photodiode is connected with a temperature compensation circuit which adjusts a bias voltage applied to the sensor photodiodes.

One advantage resides in improved temperature stabilization due to thermally equivalent environments for the detector pixel and reference avalanche photodiode.

Still further advantages and benefits will become apparent to those of ordinary skill in the art upon reading and understanding the following detailed description.

The present application may take form in various components and arrangements of components, and in various steps and arrangements of steps. The drawings are only for purposes of illustrating the preferred embodiments and are not to be construed as limiting the present application.

FIG. 1 diagrammatically shows a transmission radiation system employing a temperature compensation circuit;

Figure 1:
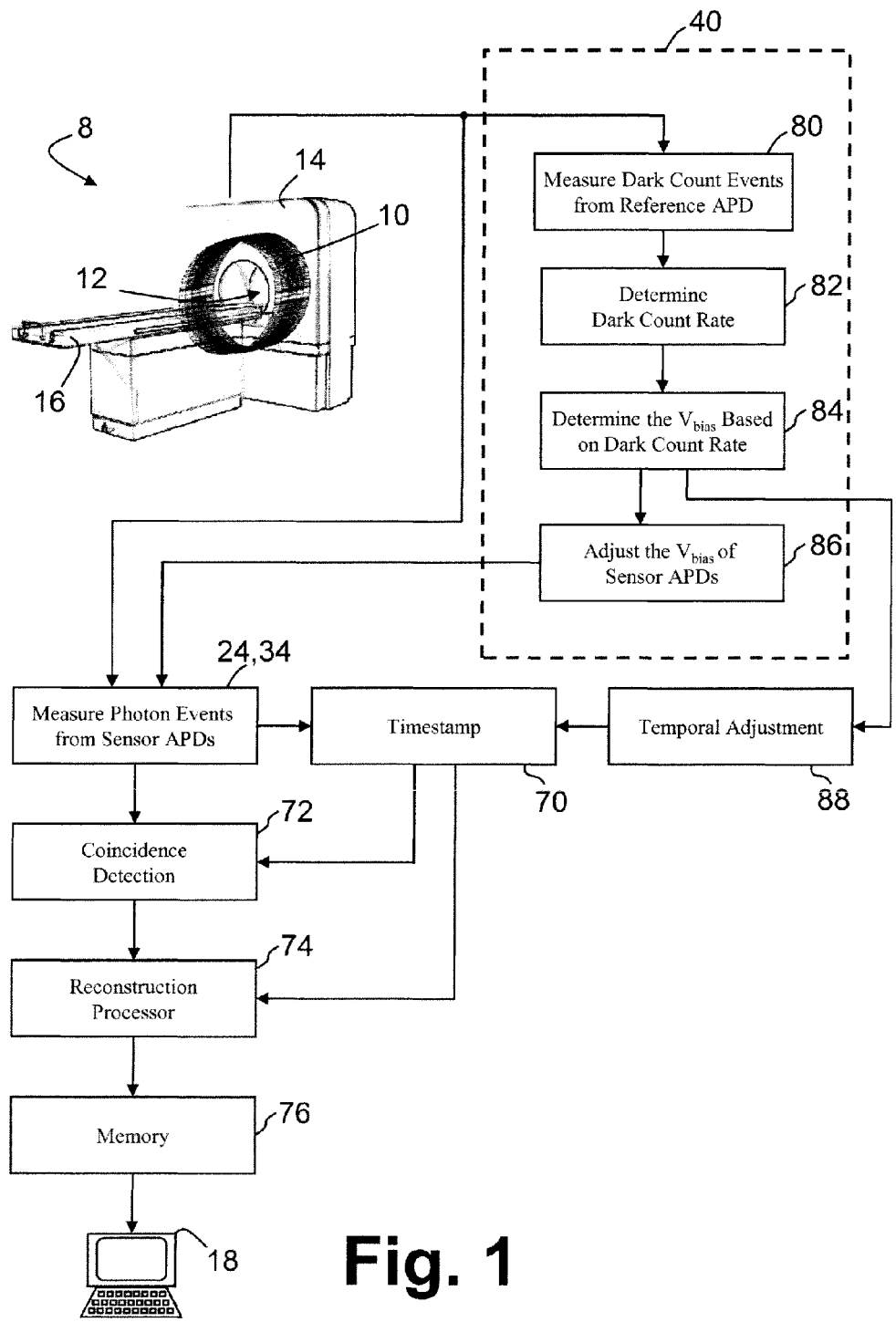

With reference to FIG. 1, a PET or other radiation tomography scanner 8 includes a plurality of radiation detector modules 10 oriented to receive radiation from an imaging region 12. In FIG. 1, the radiation detector modules 10 are arranged in several adjacent rings along an axial direction; however, other arrangements of radiation detector modules can be used. Moreover, it is to be appreciated that the plurality of radiation detector modules 10 is diagrammatically illustrated; typically the radiation detector modules 10 are housed within a housing 14 of the tomography scanner 8 and thus are not visible from the outside. Typically, each ring is comprised of hundreds or thousands of radiation detector modules 10. In some scanners, only a single ring of radiation detector modules 10 is provided, in others, up to five or more rings of radiation detector modules 10 are provided. It should be appreciated that detector heads can be used in place of the detector ring structure shown in FIG. 1. The tomography scanner 8 includes a subject support 16 for positioning an object or a human patient in the imaging region 12. Optionally, the support 16 is linearly movable in the axial direction generally transverse to the rings of the radiation detector modules 10 to facilitate acquisition of three-dimensional imaging data over an extended axial distance.

Figure 2:
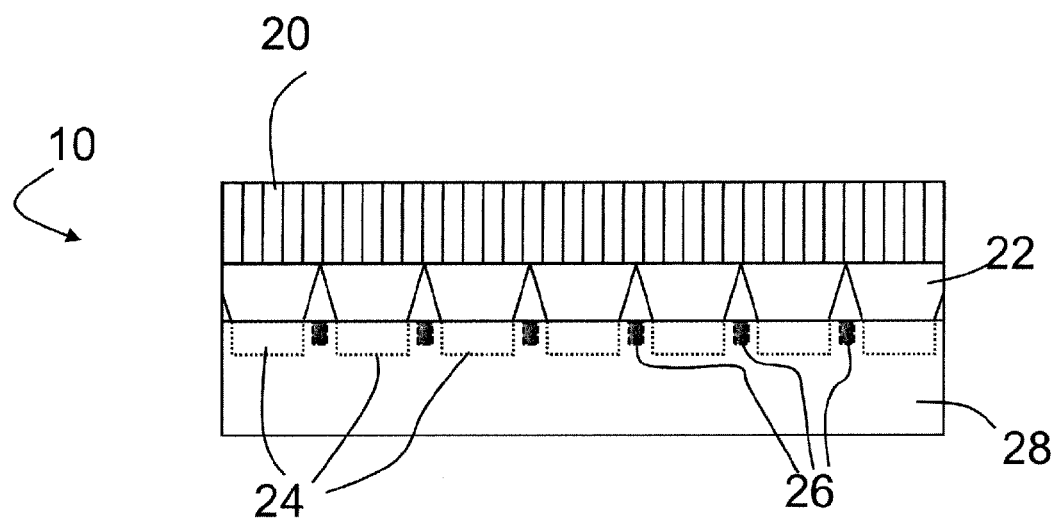
FIG. 2 shows a cross-sectional view of one embodiment of the radiation detector modules with reference diodes.

With reference to FIG. 2, a pixelated detector module 10 includes an array of scintillation crystals 20 or other scintillators. The scintillator is selected to provide high stopping power for the inducement radiation with rapid temporal decay of the scintillation burst. Some suitable materials include LSO, LYSO, MLS, LGSO, LaBr, CsI(Ti), and mixtures thereof. It should be appreciated that other scintillator materials can be used. Light guides 22 connect scintillator crystals to an array (e.g., a 1000×1000 array) of active APDs corresponding to a detector pixel 24. Reference detectors 26, such as reference APDs, are mounted among the active detector pixels 24. In the illustrated embodiment, the pixels and reference APDs are formed on a common substrate 28. In response to being struck by radiation, the scintillator crystal emits a burst of photons. The light photons strike the APDs of the detector pixel, causing them to break down and emit a pulse. The pulse has a sharp leading edge which facilitates temporal resolution. When radiation events are sparse, the pulses from each APD are counted and the sum is indicative of the amount of radiation received. Their outputs are combined to create a single, higher amplitude pulse, still with a sharp leading edge.

Figure 3:
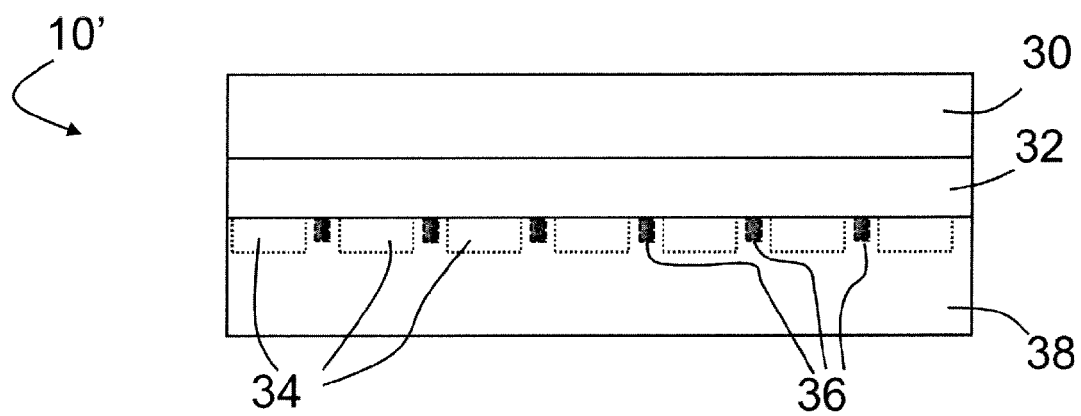
FIG. 3 shows a cross-sectional view of another embodiment of one of the detector modules.

With reference to FIG. 3, in an Anger logic embodiment, each detector module 10' includes a scintillator 30 that produces a scintillation or burst of light when radiation, such as gamma radiation, strikes the scintillator 30. The burst of light is propagated by a light guide 32 to several APDs corresponding to each detector pixel 34. Reference detectors 36, such as APDs, are formed among the detector pixel photodiodes on a common substrate 38. Under sparse radiation conditions, each radiation event causes the scintillator crystal to emit several photons of light. An APD that receives the photon triggers breakdown and generates a pulse. From the pattern of the pixels that generated a pulse, the location of the scintillation event can be determined using Anger logic.

The reference APDs 26, 36 are disposed in gaps between adjacent detector pixels 24, 34. The reference APDs 26, 36 are shielded from the photons generated by the scintillator. The shielding can be a metal or other light blocking cap disposed to shield the reference APDs 26, 36 from light. In one embodiment, a single reference APD is associated with each pixel of the detector module and disposed adjacent to that pixel. In another embodiment, multiple reference APDs 26, 36 are arranged around the perimeter of a single pixel. The output values of the reference APD are used in cooperation for accurate temperature compensation.

The sensor APDs are suitable silicon avalanche photodiodes (APD) that are biased in a Geiger-mode type of operation. This mode of operation includes reverse-biasing the APD with a bias voltage greater than the breakdown voltage such that a single photon can trigger a self-sustaining avalanche current due to impact ionization. The avalanche current, which is in the order of $10^6$ electrons per photon, will continue to flow until the bias voltage is lowered with a quenching circuit, restoring the sensor photodiode to an operative state. In one embodiment, the quenching circuit is a passive quenching circuit which is composed of a single quenching resistor which causes the avalanche current to self-quench due to a voltage drop across a large load. After the voltage bias is lowered below the breakdown voltage, it recovers allowing the APD to return to an operative or ready state. In another embodiment, the slow recovery time, or dead time, is reduced by an active quenching circuit in which an electronic circuit, e.g., a CMOS or TTL, detects the rising edge of the avalanche current and rapidly lowers bias by applying a quenching pulse to the APD, then quickly switches the voltage bias back to Geiger-mode operation. A photon counter (not shown) counts the instances of avalanche current within a predefined time period.

In one embodiment, the reference APDs 26, 36 are identical to the sensor APDs that make up pixels 24, 34, with the exception of a light blocking cap that shields the reference APD from the photons produced by the scintillator 20, 30. Instead of detecting photo-generated electron-hole pairs, the reference APD detects thermally generated electron-hole pairs or dark current. Each reference APD 26, 36 is similarly connected to the passive or active quenching circuit, in order to ensure high speed detection of thermally generated dark current.

Thermally generated electron-hole pairs are created by generation-recombination processes within the semiconductor and can trigger an avalanche current in the absence of a photon. As the name suggest, thermally generated electron-hole pairs are temperature dependent, changes in the temperature cause changes in the breakdown voltage because the crystal lattice vibration is directly proportional to the temperature causing electron-hole pairs to collide with the lattice before reaching an energy level sufficient to trigger avalanche current. The thermally generated avalanche current, known as dark current, is a source of noise in the sensor APDs of pixels 24, 34 by causing false triggers. The number of thermally generated electron-hole pairs can be reduced by lowering the temperature. This can improve signal-to-noise (SNR) at the expense of system complexity and cost. Further degradation of sensor performance due to a temperature induced drift of the breakdown voltage can be prevented by maintaining a constant temperature within +/−0.1° K along with a predetermined temperature offset corresponding to the constant temperature. This method of controlling the system temperature increases demand on the cooling system and adds to the manufacturing and operating costs.

Figure 4:
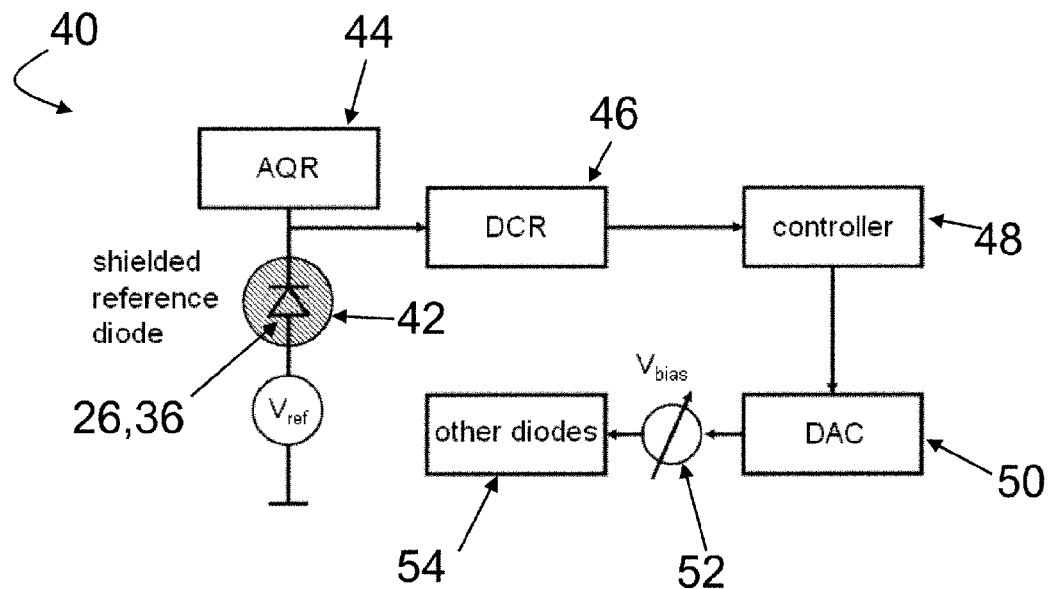
FIG. 4 shows a general control diagram of one of the temperature compensation circuits.

With reference to FIG. 4, a temperature compensation circuit 40 compensates for temperature changes by using the dark current from the reference APDs 26, 36 to adjust a voltage bias to maintain a constant breakdown excess in the sensor APDs of pixels 24, 34. In one embodiment, the shielded reference APD 26, 36, which is enclosed in a light opaque housing 42, is electrically connected to an active quenching circuit 44. The dark count rate is calculated by a gated counter 46 configured to detect and count the quenching pulse of active quenching circuit 44 during a predefined time period. In another embodiment, the gated counter 46 is configured to detect the rising edge of the avalanche current instead of the quenching pulse outputted from the active quenching circuit 44. It should also be appreciated that other types of digital counters can be used in place of the gated counter. The gated counter 46 outputs a digital value representative of the dark count rate to the input of a controller 48. In one embodiment, the controller employs a look-up table to cross reference the dark count rate with the adjusted voltage bias. In another embodiment, the controller uses a control loop algorithm to determine the adjusted voltage bias. The controller 48 outputs a digital value representative of the adjusted voltage bias to an input of a digital-to-analog converter 50 which converts the adjusted digital voltage bias value to an analog signal and outputs the analog adjusted voltage bias to a variable voltage source 52, e.g. a charge pump. The variable voltage source 52 is configured to adjust the voltage bias across the sensor APDs 54 based on the output of the controller 48.

Figure 5:
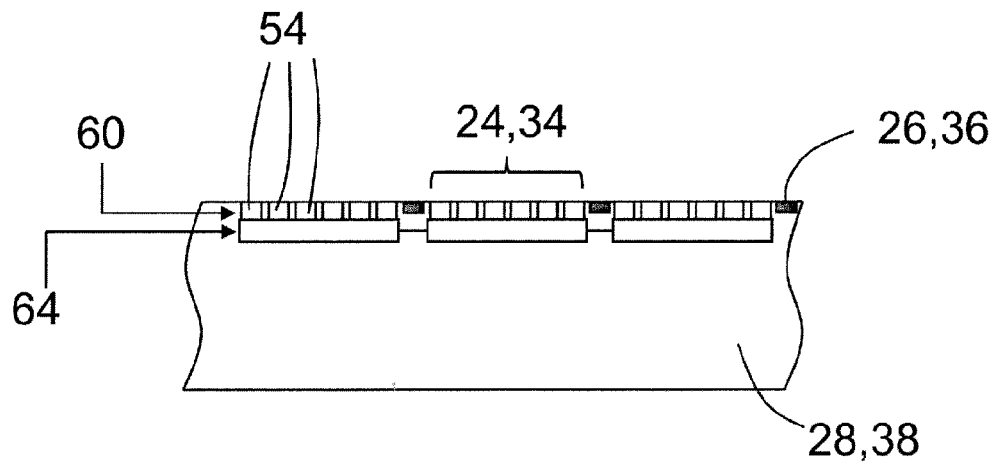
FIG. 5 shows a cross-sectional view of one physical layout embodiment of the radiation detector module, in which sensor APDs, and reference APDs are disposed in a photodiode layer, and temperature compensation circuit and digital circuitry are disposed in a digital circuitry layer separate from and electrically coupled with the photodiode layer.

With reference to FIG. 5, in one embodiment the silicon substrate 28, 38 has at least two layers. The first layer is the photodiode layer 60 which includes the APDs 54 arranged in arrays that form each of a plurality of pixels 24, 34. The reference APDs 26, 36 are disposed in a gap, e.g., a 100 µm gap, between adjacent pixels 24, 34. In a separate layer, a digital circuitry layer 64, which is electronically connected to the photodiode layer 60, is comprised of digital circuitry responsible for outputting photon detection specific information such as radiation detector module identification, pixel identification, timestamps, and photon counts. The digital circuitry may also include digital biasing circuitry, digital triggering circuitry, and readout circuitry. The temperature compensation circuit(s) 40, in one embodiment, are also disposed in the digital circuit layer 64. In one embodiment, a digital compensation circuit is provided for the APDs of each pixel. In another embodiment, one temperature compensation circuit adjusts the bias of all APDs on the substrate 28, 38 except the reference APDs.

The pixels 24, 34 are arranged in a two dimensional array to define a light sensitive surface of the radiation detector module 10, 10'. Interspersed among the detector pixels are disposed the reference APDs 26, 36 in a gap between adjacent pixels 24, 34. Various physical layouts can be used.

Figure 6:
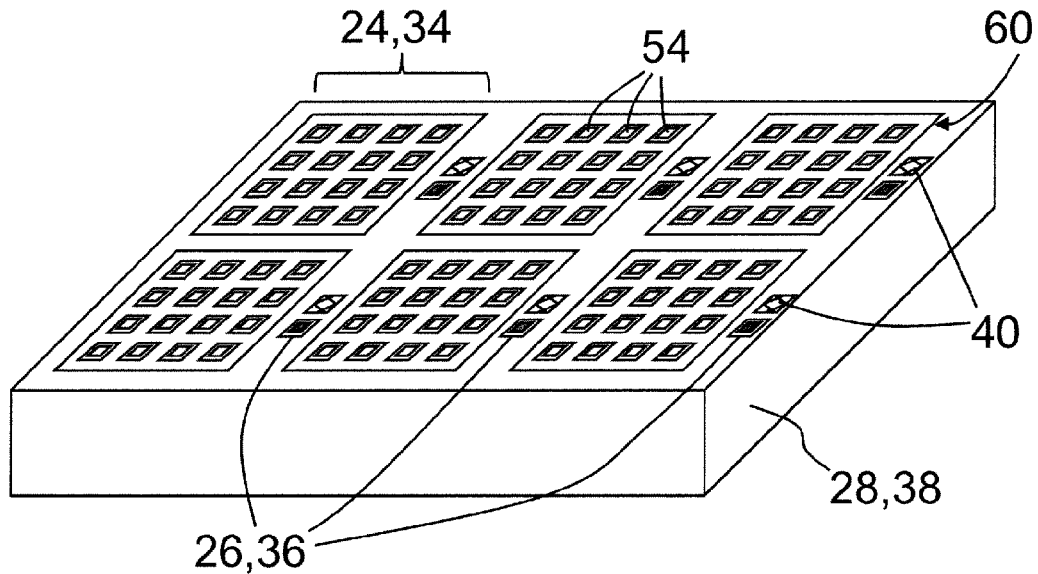
FIG. 6 shows a perspective view of another embodiment of a radiation detector module with sensor APDs, reference APDs, and temperature compensation circuits.

In an embodiment shown in FIG. 6, the temperature compensation circuits 40 are disposed in the photodiode layer 60 in the gap between pixels 24, 34.

Figure 7:
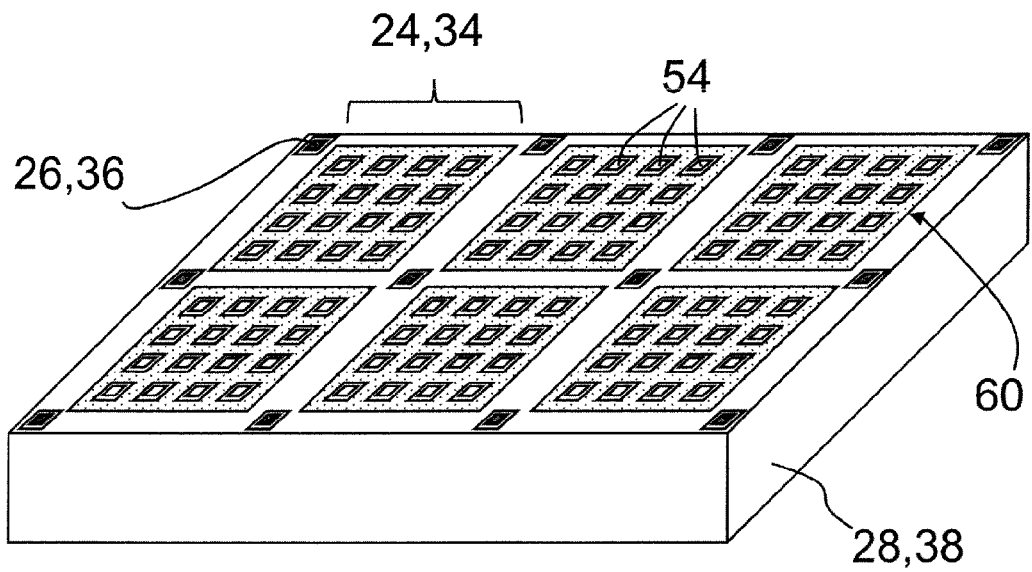
FIG. 7 shows a perspective view of another embodiment of a radiation detector module, in which the reference APDs are disposed adjacent corners of each pixel; and, FIG. 8 shows a perspective view of another embodiment of a radiation detector module, in which reference APDs are disposed in gaps between sensor APDs within a single pixel.

In an embodiment as shown in FIG. 7, the reference APDs 26, 36 are disposed adjacent the corners of each pixel 24, 34. Each reference APD is connected with a dark current rate counter 46. The controller 48 for each pixel 24, 34 averages the counters from the four reference APDs at the corners of the corresponding pixel. It should be appreciated that other mathematical algorithms may be employed such as gradient operators, adaptive averaging or outlier detection.

Figure 8:
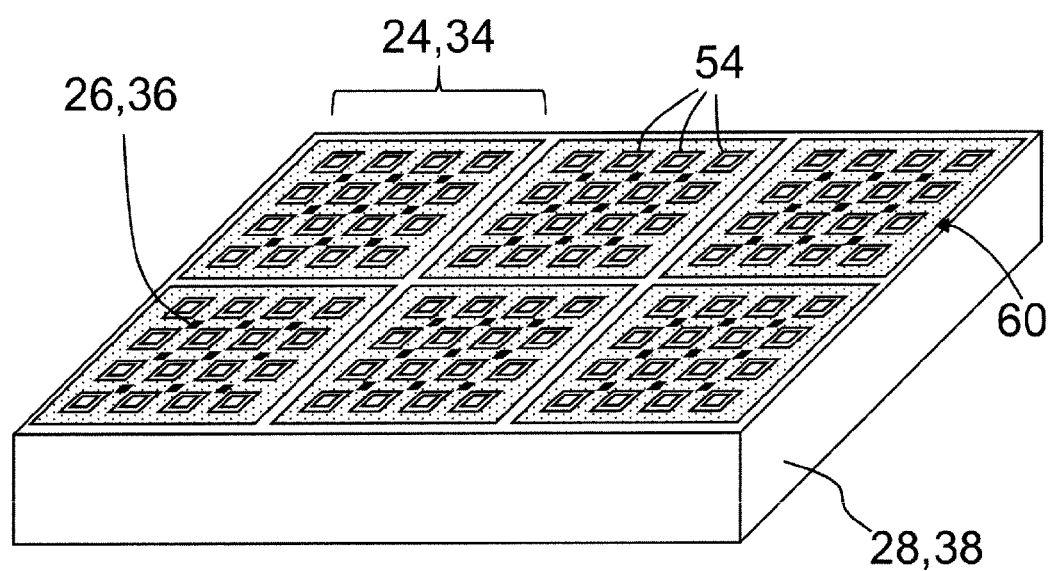

In another embodiment shown in FIG. 8, the reference APDs 26, 36 are disposed between sensor APDs 24, 34, within each pixel 24, 34. In another embodiment, one (or more) of the APDs in the array corresponding to each pixel is shielded from light from the scintillator and used as the reference APD. In another embodiment, the reference detectors 26, 36 are other thermal sensors, such as thermistors.

In another embodiment, the scanner is a TOF-PET scanner. The controller 48 also generates, e.g., by accessing a temporal correction look-up table, a temperature-dependent temporal correction for the time stamp corresponding to each event.

In another embodiment, the controller 48 also generates, e.g. by accessing a photon count correction look-up table, a temperature-dependent photon count correction for the photon count corresponding to each event.

With reference again to FIG. 1, a patient on the support 16 is injected with a radiopharmaceutical. Radiation events are detected by the sensor APDs 54 of the pixels 24, 34 of the detector modules 10. A time stamp is associated with each sensed scintillation event by a time stamp circuit 70. A coincident detector 72 determines coincident pairs and the LOR defined by each coincident pair. A reconstruction processor 74 reconstructs the LORs into an image representation which is stored in an image memory 76. In a TOF-PET system, the reconstruction processor also receives time-of-flight information for each LOR from the time-stamp circuit 70.

As the sensor APDs 54 of the pixel 24, 34 detect radiation events, the temperature compensation circuit(s) 40 of each detector module 10 measure 80 the dark current events from their respective reference APDs and determine 82 the dark count rate. The temperature corrected bias voltage for the sensor and reference APDs of the module is determined 84 and the temperature corrected bias voltage is applied 86 to the sensor APDs, as well as the reference APDs. In a TOF-PET scanner, temporal adjustment is determined 88 and applied to the time-stamp circuit.

The present application has been described with reference to the preferred embodiments. Modifications and alterations may occur to others upon reading and understanding the preceding detailed description. It is intended that the present application be construed as including all such modifications and alterations insofar as they come within the scope of the appended claims or the equivalents thereof.

Having thus described the preferred embodimemts, the invention is now claimed to be:

1. A radiation detector module for use in diagnostic imaging, the detector module comprising:
    at least one detector pixel, each detector pixel including a scintillator optically coupled to one or more sensor APDs that are biased in a breakdown region in a Geiger-mode, the sensor APDs being configured to output a current pulse in response to light from the scintillator corresponding to a single incident radiation photon;
    at least one reference detector configured to output a temperature dependent signal, the reference detector including:
        at least one reference APD biased in a breakdown region in the Geiger mode and configured to output a current pulse in response to each breakdown event triggered by a thermal generation of an electron-hole pair;
    at least one temperature compensation circuit configured to adjust a voltage bias applied to the sensor APDs based on the temperature dependent signal.

2. The radiation detector according to claim 1, wherein the at least one reference APD is optically isolated such that the output of the at least one APD is independent of light output by the scintillator.

3. The radiation detector module according to claim 2, further including:
    an active or passive quenching circuit coupled with the at least one reference APD which quenches the at least one reference APD after each breakdown event such that the at least one reference APD outputs a series of pulses at a rate which is indicative of temperature.

4. The radiation detector module according to claim 3, wherein the temperature compensation circuit further includes:
    a gated counter connected to at least one corresponding reference APD to receive output pulses therefrom and configured to output a dark current count rate for the at least one corresponding reference APD;
    a controller configured to output a control signal based on the dark count rate;
    a variable voltage source configured to adjust the voltage bias applied to corresponding sensor APDs; and
    wherein the reference APD is statically biased.

5. The radiation detector module according to claim 4, wherein the controller outputs a digital control signal which is (i) determined from an algorithm that incorporates the dark count rate in a formulation, or (ii) determined from a look-up table that associates the dark count rate with a corresponding output and further including:
    an analog-to-digital converter which converts the digital signal to an analog control signal that is applied to the variable voltage source.

6. The radiation detector module according to claim 2, wherein each reference APD is disposed in a gap between adjoining pixels.

7. The radiation detector module according to claim 2, wherein the sensor APDs, the reference APDs, and the at least one temperature compensation circuit are disposed monolithically on a common silicon substrate.

8. A plurality of the detector modules according to claim 1, in which the modules are mounted in a close-packed array.

9. The plurality of detector modules according to claim 8, wherein each module is rectangular and the modules are mounted in a rectangular array.

10. A PET scanner including:
    a plurality of the radiation detection modules according to claim 2, geometrically arranged about an imaging region;
    a coincidence detector which detects pairs of detected radiation events and determines lines of response corresponding to the coincident pairs; and
    a reconstruction processor which reconstructs the lines of response into an image representation.

11. The PET scanner according to claim 10, wherein the sensor APDs of each detector module further includes a time stamp circuit which associates a time stamp(s) with the pulses from the pixels and wherein the temperature compensation circuit is further configured to temporally adjust the time stamp circuit based on the temperature dependent signal.

12. A method of compensating for temperature changes of a radiation detector module used in diagnostic imaging, the method comprising:
generating output pulses from pixels, each pixel including at least one sensor APD which is biased in a breakdown region in a Geiger mode in response to light from an associated scintillator causing one or more of the sensor APDs to break down;
with a reference APD biased in a breakdown region in the Geiger mode and shielded from light, generating a temperature dependent dark current based on thermally generated electron hole pairs;
adjusting a bias voltage applied to the sensor APDs based on the temperature dependent dark current.

13. The method according to claim 12, further including:
periodically quenching the reference APD; and
counting a pulse rate of the dark current.

14. The method according to claim 13, further including:
converting the counted pulse rate into a bias voltage;
applying the bias voltage to the sensor APDs.

15. A method of making a radiation detector module comprising:
forming an array of APDs;
optically coupling sensor APDs with scintillators;
optically shielding at least one reference APD;
mounting the optically shielded at least one reference APD to the scintillator, the at least one reference APD being optically shielded from the scintillator;
biasing the sensor and reference APDs to a breakdown region in a Gieger mode such that the sensor APDs breakdown in response to light from the scintillators and the at least one reference APD breaks down in response to a thermal generation of an electron-hole pair;
quenching the sensor and reference APDs which break down such that the sensor APD generates a series of pulses indicative of light received from the scintillators and the least one reference APD generates a series of pulses indicative of temperature;
connecting the optically shielded reference APD with a temperature compensation circuit which adjusts a bias voltage applied to the sensor APDs based on the series of pulses from the at least one reference APD.

16. The method according to claim 15, wherein the array of sensor APDs are formed with a gap between pixels and the at least one reference APD is formed in the gap.

17. The method according to claim 15, wherein a plurality of the optically shielded reference APDs are defined among the APDs which are coupled to the scintillators.

18. A radiation detector module for use in radiation emission tomography, the detector module comprising:
at least one monolithically disposed detector pixel, each detector pixel including a scintillator optically coupled to one or more sensor APDs that are biased in a breakdown region in a Geiger-mode and connected with quenching circuits, the sensor APDs being optically coupled to the scintillator and configured to output a current pulse in response to light from the scintillator corresponding to a single incident radiation photon;
at least one monolithically disposed reference APD optically isolated from the scintillator, statically biased in a breakdown region in the Geiger mode, and configured with at least one quenching circuit to output a current pulse in response to each breakdown event triggered by a thermal generation of an electron-hole pair;
at least one monolithically disposed temperature compensation circuit configured to determine a corrected voltage bias based on a rate of the thermally generated break down events; and
at least one monolithically disposed variable voltage source configured to adjust the voltage bias applied to sensor APDs to apply the corrected voltage bias determined by the temperature compensation circuit.

* * * * *